(12) United States Patent
Kiesele et al.

(10) Patent No.: US 7,615,139 B2
(45) Date of Patent: Nov. 10, 2009

(54) ELECTROCHEMICAL SENSOR

(75) Inventors: Herbert Kiesele, Lübeck (DE); Frank Mett, Lübeck (DE); Sabrina Sommer, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 690 days.

(21) Appl. No.: 11/269,184

(22) Filed: Nov. 8, 2005

(65) Prior Publication Data
US 2006/0237313 A1    Oct. 26, 2006

(30) Foreign Application Priority Data
Dec. 23, 2004   (DE)   .................. 10 2004 062 052

(51) Int. Cl.
*G01N 27/26* (2006.01)
*G01N 17/00* (2006.01)

(52) U.S. Cl. .................. 204/412; 204/406; 204/411; 204/415; 204/431; 204/432; 204/435; 205/775

(58) Field of Classification Search ................. 204/411, 204/412, 450, 415, 406, 431, 432, 435; 205/775
See application file for complete search history.

(56) References Cited

U.S. PATENT DOCUMENTS

| | | | | |
|---|---|---|---|---|
| 4,925,544 A | * | 5/1990 | Goldring | 204/421 |
| 5,540,828 A | * | 7/1996 | Yacynych | 205/198 |
| 5,645,709 A | * | 7/1997 | Birch et al. | 205/775 |
| 6,024,853 A | * | 2/2000 | Kiesele et al. | 204/412 |

FOREIGN PATENT DOCUMENTS

| | | |
|---|---|---|
| DE | 42 31 256 A1 | 3/1994 |
| DE | 43 02 323 | 8/1994 |
| DE | 197 26 453 | 1/1999 |
| DE | 198 45 318 | 4/2000 |
| DE | 199 39 011 | 1/2001 |
| DE | 101 44 862 | 3/2003 |
| EP | 0 096 417 | 12/1983 |
| GB | 2 066 965 A | 7/1981 |
| GB | 2342168 | 4/2000 |
| RU | 2249203 | 3/2005 |

(Continued)

OTHER PUBLICATIONS

Zhong Zhu et al., Electrochemical characteristics of boron-doped polycrystalline diamond film electrodes, 1995, Springer-Verlag, Fresenius Journal Analytical Chemistry, 352 : 389-392.*

(Continued)

*Primary Examiner*—Brian J Sines
*Assistant Examiner*—Jennifer Dieterle
(74) *Attorney, Agent, or Firm*—McGlew and Tuttle, P.C.

(57) ABSTRACT

An electrochemical sensor with at least one measuring electrode (3), at least one auxiliary electrode (7) and at least one reference electrode (5), wherein a protective electrode (6), which ensures at the reference electrode (5) the at least partial shielding of the reference electrode (5) against substances that would lead to a change in the reference potential when reaching the reference electrode (5), is arranged in the vicinity of the reference electrode (5). A highly stable reference potential can be obtained with the present invention.

16 Claims, 8 Drawing Sheets

FOREIGN PATENT DOCUMENTS

WO      WO 99/01757      1/1999

OTHER PUBLICATIONS

Sotiropoulou et al., Carbon nanotube array-based biosensor, Oct. 2002, Springer-Verlag, Analytical Bioanalytical Chemistry, 375 : 103-105.*

Lam et al., Screen-printed transcutaneous oxygen sensor employing polymer electrolytes, 2003, Medical & Biological Engineering & Computing, vol. 41,456-463.*

McGlew, Proposed Amendment, Memo, Jun. 12, 2009 (Attorney documentation of Jun. 10, 2009 phone conversation, see interview summary).*

Sotiropoulou, S.; Gavalas, V.; Novel Carbon Materials in Biosensor Systems. In: Biosensors and Bioelectronics, 2003, vol. 18, S. 211-215.

Jian-Bo H.; Study of Multi-Wall Carbon Nanotubes Self-Assembled Electrode and its Application to the Determination of Carbon Monoxide; In: Sensors and Actuators B, 2004, vol. 99, S. 1-5.

* cited by examiner

ELECTROCHEMICAL SENSOR

CROSS REFERENCE TO RELATED APPLICATIONS

This application claims the benefit of priority under 35 U.S.C. § 119 of German Application DE 10 2004 062 052.0 filed Dec. 23, 2004, the entire contents of which are incorporated herein by reference.

FIELD OF THE INVENTION

The present invention pertains to an electrochemical sensor, mainly a sensor to be operated amperometrically, with at least one measuring electrode, at least one auxiliary electrode and at least one reference electrode. Such three-electrode sensors are used for qualitative and quantitative measurements of various gases.

BACKGROUND OF THE INVENTION

Conversion of the substance to be detected takes place in electrochemical sensors during the measurement of gases, and the conversion can be evaluated in a qualified manner on the basis of changes in potential at the measuring electrode (frequently called working electrode) and/or due to currents flowing through the electrochemical sensor. The information content of the measurement results obtained can be considerably increased if a third electrode is used as a reference electrode, which is the case in common three-electrode sensors. This third electrode has no current load, as a result of which a so-called "open circuit potential" (OCP) is formed at this electrode. This OCP is used as a reference potential for one or more measuring electrodes. The sensors are actuated mostly by so-called potentiostats, which maintain the potential difference between the measuring electrode and the reference electrode at a constant value, while the current flow is measured between the measuring electrode and the auxiliary electrode.

To obtain the "open circuit potential" as a reliable reference potential, it is to be ensured that processes taking place in the sensor will affect this reference potential as little as possible. Such an effect can occur due to various processes. For example, reaction products formed at the measuring electrode or auxiliary electrode may diffuse to the reference electrode and cause changes in the reference potential. $H^+$ and $OH^-$ can be primarily considered to be such reaction products. So-called mediators are frequently also used in electrochemical sensors. Mediators are ions or molecules that transfer electrons between the analyte and electrodes and are usually selected to be such that they react with the analyte as selectively as possible. Reduced or oxidized mediator molecules or ions, which diffuse into the vicinity of the reference electrode and may lead to potential change there, also occur in this case. Analyte and/or interfering accompanying gases may reach the reference electrode in case of high gas concentrations and bring about a corresponding change in potential. This risk occurs, for example, in case of high CO concentrations as a consequence of fires. The decomposition of organic electrolyte solution may likewise lead to disturbances and long-lasting poisoning of the reference electrode.

Besides general requirements on a reference electrode, such as the simplest manufacture possible, or environmental friendliness, the lowest possible toxicity and good ability to be disposed of, a number of electrochemical requirements are to be imposed on reference electrodes. These include the stable design of the electrochemical reference potential and extensive independence of this reference potential from changes in the pH and $pO_2$ values. Furthermore, the susceptibility to interferences and poisoning phenomena on the electrode surface, which can be caused by electrochemical reaction products or interfering gases from the electrolyte, must be as low as possible.

Various approaches to designing reference electrodes in three-electrode electrochemical sensors have been known, but they all meet the requirements described only partially.

A reference electrode of this class is known from DE 42 31 256 A1. The type of reference electrode disclosed there comprises a reference electrode made of a catalytically active precious metal, on the surface of which oxide is formed. Platinum/platinum oxide electrodes and iridium/iridium oxide electrodes are frequently used. These electrodes are characterized by simple manufacture and the stable design of a reference potential and are nontoxic or only slightly toxic. Their drawback is the high susceptibility to poisoning phenomena as well as the possibility that the reference potential can be affected by changing $pO_2$ and pH values in the electrolyte environment.

Other known reference electrodes according to the state of the art are so-called reference electrodes of the first kind, in which a metal or a soluble phase is at equilibrium with a corresponding ion. The best-known example of this is the so-called hydrogen electrode.

Another approach from the state of the art is the use of a reference electrode of the second kind, which is characterized by a metal, which is at equilibrium with a poorly soluble metal salt. Mercury/mercury sulfate electrodes (GB 2 066 965 A) and silver/silver chloride electrodes (WO 99 01 757 A1) shall be mentioned as examples here. All the above-mentioned reference electrodes according to the state of the art have, on the whole, an excessively strong tendency to show interference phenomena with toxic gases.

SUMMARY OF THE INVENTION

The object of the present invention is to provide a three-electrode electrochemical sensor with a more stable reference potential compared to the state of the art.

The present invention comprises an electrochemical sensor with at least one measuring electrode, at least one auxiliary electrode and at least one reference electrode, wherein a protective electrode is arranged in the vicinity of the reference electrode such that it ensures at the reference electrode at least a partial shielding of the reference electrode against substances that would lead to a change in the reference potential when reaching the reference electrode. The shielding of the reference electrode according to the present invention can be combined with other measures for stabilizing the reference potential.

The present invention is based on the fact that penetration of the substance to be detected into the interior of the electrochemical sensor and consequently into the electrolyte volume cannot be ruled out completely even during the measurement. Thus, substances to be detected may lead to changes at the reference electrode, besides the electrochemical conversion taking place at the measuring electrode. However, changes in the electrode properties of the reference electrode cause a change in the reference potential, which is to be avoided under any circumstances. The approach according to the present invention is based now on the fact that an electrode located in the immediate vicinity of the reference electrode, which shows electrochemically an action similar to that of the measuring electrode itself, brings about conversion of the substances to be detected in the immediate vicinity of the reference electrode, which leads to depletion of these substances in the immediate environment of the reference electrode. The reference electrode is thus protected against the effect of the substances to be detected, regardless of how these substances have arrived in the vicinity of the reference electrode. To guarantee the electrochemical activity of the protective electrode that recreates the action of the measuring electrode, it is especially advantageous if this protective electrode is maintained at a potential that deviates from the potential at which the measuring electrode is maintained by at most +/−100 mV, a potential that is slightly increased in relation to the measuring electrode being advantageous if an oxidation essentially takes place, or a slightly lowered potential in relation to the potential of the measuring electrode being advantageous if a reduction essentially takes place. Substances that could otherwise lead to poisoning of the reference electrode or to a parasitic conversion at the reference electrode, which would lead to an effect on the reference potential, are effectively depleted as a result. It is not necessary for this for the protective electrode to have the same selectivity as the measuring electrode. It may be advantageous to use materials that make possible the conversion of the greatest possible number of interfering components for the protective electrode.

Furthermore, it may be advantageous to combine the protection of the reference electrode by a protective electrode maintained approximately at the potential of the measuring electrode with other protective mechanisms. Thus, it may be advantageous for the surface of the reference electrode to be partially covered with a material that has a barrier action against substances that would lead to a change in the reference potential when reaching the reference electrode. An advantageous selective barrier action can also be achieved by the use of ion exchange membranes in case of the use of ionic mediators.

The application of materials with a desired barrier action can be advantageously embodied by applying the reference electrode to a plastic carrier, which seals the reference electrode at least on one side. It is now sufficient for the effective protection of the reference electrode if a protective electrode is located in front of the unsealed side of the reference electrode. The arrangement according to the present invention can be embodied especially advantageously if the reference electrode is nearly completely surrounded by a protective electrode that is permeable to the electrolyte. For example, a conventional metal/metal oxide electrode can be used as the reference electrode in such an arrangement, in which case the electrode material can be applied to a substrate that is permeable to the electrolyte. In case of the use of an electrolyte-proof substrate as the electrode carrier, the substrate should be provided with perforations to make possible the continuous exchange of electrolyte. A precious metal such as platinum, iridium or a similar material, which is applied to a nonwoven (nonwoven material/fabric) that is permeable to the electrolyte according to the thin-layer or thick-layer technique, is advantageously used as the protective electrode. An advantageous embodiment of an electrochemical sensor contains a form of the reference electrode in which the reference electrode is integrated in a stack of layers that contains alternatingly layers of the material of the reference electrode and layers of the material of the protective electrode, the outer limitation of the stack of layers being formed by layers of the material of the protective electrode. If such a stacked arrangement has a sufficiently large surface and it is directed at right angles to the principal direction of diffusion, the analyte or its decomposition products are at the same time prevented by the sandwich-like electrode arrangement from reaching the auxiliary electrode and conversely, the products formed at the auxiliary electrode are thus prevented from reaching the measuring electrode. The so-called "cross-talk" between the measuring electrode and the auxiliary electrode is thus effectively reduced.

In another advantageous embodiment of an electrochemical sensor, one layer of the material of the protective electrode and at least one layer of the material of the reference electrode are rolled up in the form of a so-called "Swiss roll," the outer limitation of the helical roll structure being likewise formed by a layer of the material of the protective electrode. It is especially advantageous if a layer of nonwoven, which ensures a two-dimensional contact of both electrodes with the electrolyte, is located between the protective electrode and the reference electrode. The entire roll structure is used as a reference electrode according to the present invention in electrochemical sensors.

The embodiment of an electrochemical sensor as an arrangement of concentric cylinder electrodes may be advantageous as well.

The present invention can be used especially advantageously in flat sensors with nearly two-dimensional diffusion paths. If the protective electrode is placed such that it blocks the diffusion paths to the reference electrode for substances affecting the reference potential, nearly complete shielding of the reference electrode against these substances can also be brought about without the reference electrode being enveloped by the protective electrode. Various coplanar electrode geometries can be equipped with a protective electrode according to the present invention in this advantageous manner.

Various electrode materials may be considered for embodying the reference electrode. It is advantageous to manufacture the reference electrode from a catalytically active precious metal with an oxide layer present on its surface.

In another advantageous embodiment, the reference electrode consists of diamond-like carbon or doped diamond, for example, boron-doped diamond, or carbon-based nanotubes, so-called "carbon nanotubes." "Carbon nanotubes" offer an especially large effective electrode surface. Such carbon-based electrodes make it necessary to add a so-called electrode transfer catalyst or mediator to the electrolyte. The reduction of oxygen and the oxidation of hydrogen are very strongly inhibited at such electrodes, and their potential is therefore almost independent from the pH or $pO_2$ value of the electrolyte solution. If certain mediators are added to the electrolyte solution, the electrode potential becomes established essentially as a function of the type of the mediator. It is now a mediator-specific electrode potential, which is nearly independent from the pH and $pO_2$ values. The selection of the mediator is therefore of special significance. The mediator should advantageously be selected such that the potential of the reference electrode will be determined essentially by the mediator. The advantage of carbon-based electrode materials is, besides a weak susceptibility to poisoning and interference, which arises in combination with selectively acting mediators, the high degree of independence from variations in the pH and $pO_2$ values in the electrolyte environment.

It is especially advantageous concerning the manufacture and the effective implementation of the principle according to the present invention if the measuring electrode and the reference electrode in the electrochemical sensor consist of the same material.

If a mediator is used, this is advantageously selected to be such that it reacts as selectively as possible with the gas to be detected by the particular electrochemical sensor. For example, copper chloride in an aqueous lithium chloride solution reacts selectively with sulfur dioxide.

If boron-doped diamond, diamond-like carbon or "carbon nanotubes" are used as the material for the measuring electrode and the reference electrode, the same OCP becomes established at equilibrium at both electrodes.

Due to the use of the same material for the measuring electrode and the reference electrode, it is possible to advantageously utilize the circumstance that an absolutely identical temperature curve is present in this case, as a result of which compensation measures can be omitted.

Another advantage of carbon-based reference electrodes is the extensive insensitivity to electromagnetic interferences.

The present invention will be explained in greater detail on the basis of exemplary embodiments. The exemplary embodiments pertain to possible geometric embodiments of sensors according to the present invention.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
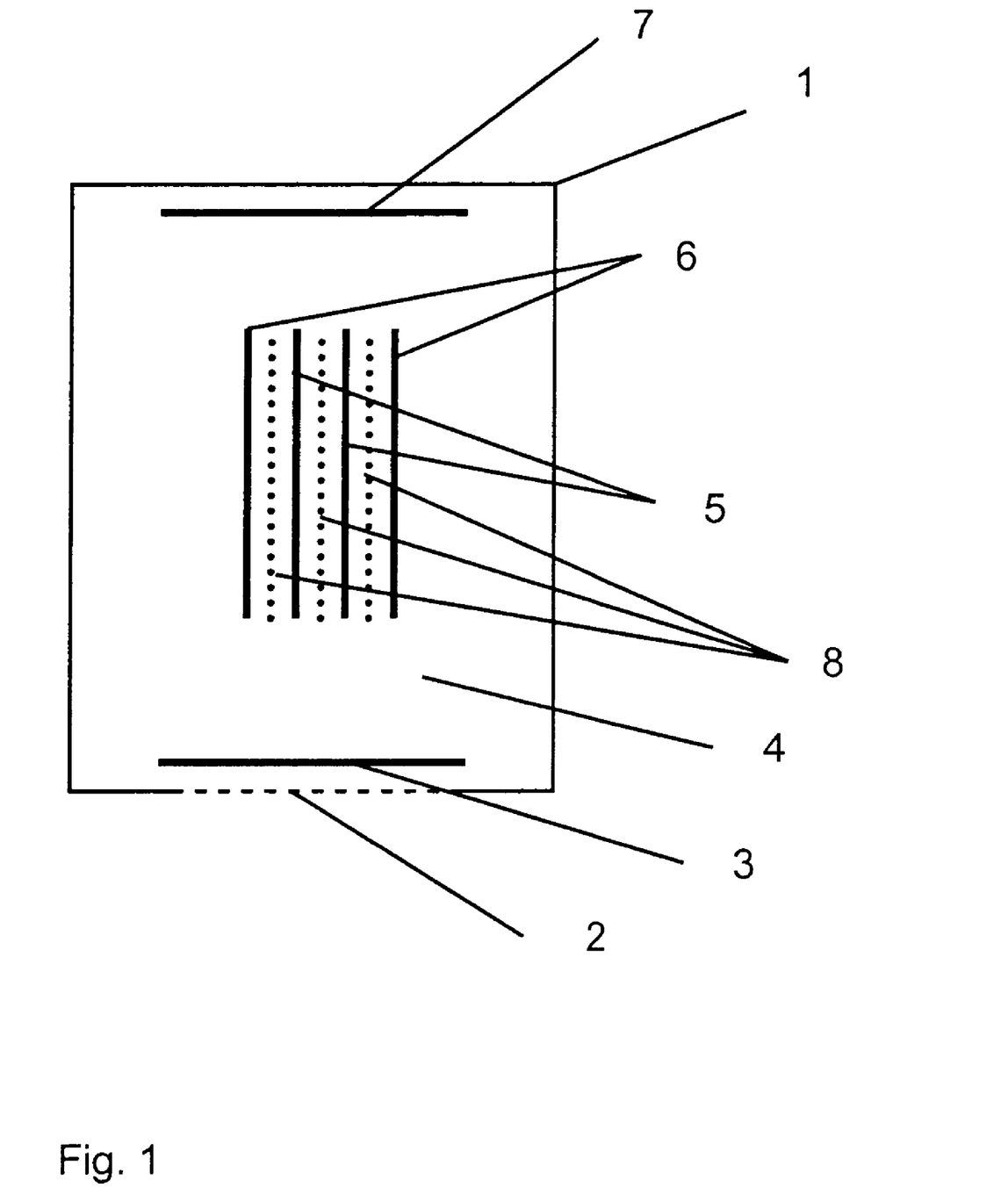
FIG. 1 is a schematic sectional view through a three-electrode sensor according to the present invention with a reference electrode designed as a "Swiss roll" structure.

Referring to the drawings in particular, the embodiment of FIG. 1 is a three-electrode electrochemical sensor according to the present invention comprising a housing 1, in which an opening is closed by a membrane 2, which is open for diffusion and behind which a measuring electrode 3 is located. A reference electrode, which is designed as a "Swiss roll," structure is arranged in the central area of the electrolyte space 4, the reference electrode containing at least one layer of a material of a reference electrode 5 and a layer of a material of a protective electrode 6, the two materials being rolled around each other and the material of the protective electrode 6 closing off the overall arrangement to the outside and toward the electrolyte space 4. A counterelectrode or auxiliary electrode 7 is arranged on the side of the sensor housing 1 facing away from the measuring electrode 3. Layers of nonwoven material 8 are arranged between the layers of the material of the reference electrode 5 and the layers of the material of the protective electrode 6, so that an intimate contact is guaranteed between the electrolyte and the electrode material. In the immediate vicinity of the reference electrode 5, the layers of the protective electrode 6 surrounding the reference electrode 5 ensure the depletion of substances that could lead to a change in potential at the reference electrode. However, diffusion-controlled migration of gaseous components to be detected and of reaction products from the measuring electrode 3 to the auxiliary electrode 7 is possible at a greater distance from the reference electrode 5 according to the present invention. Such a diffusion effect is effectively stopped only if the reference electrode is arranged such that an appreciable reduction of the cross section available for the diffusion of the substances to be detected takes place.

Figure 2:
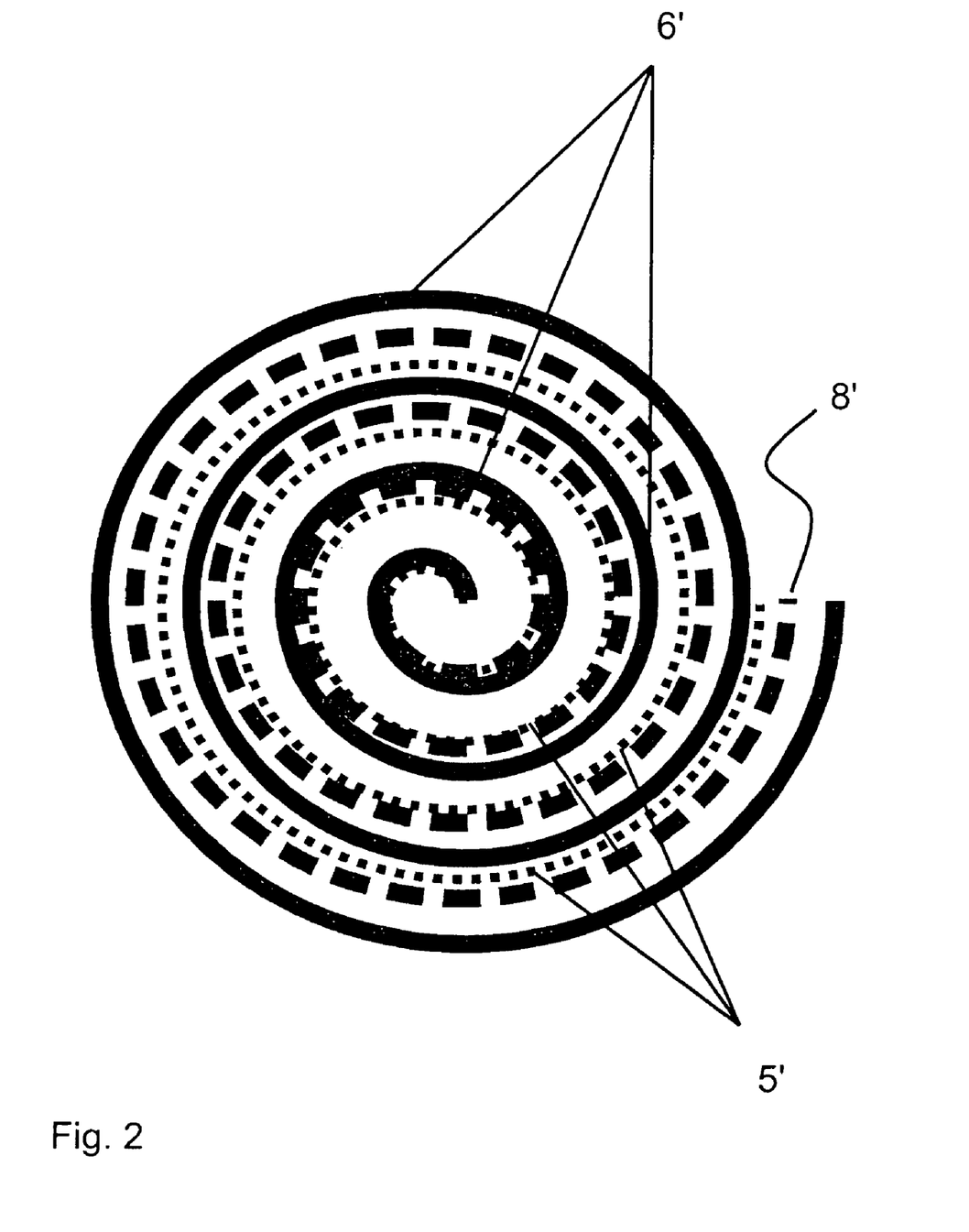
FIG. 2 is a schematic sectional view through a reference electrode designed as a "Swiss roll" structure.

FIG. 2 shows a sectional view through a reference electrode according to the present invention designed as a "Swiss roll" structure. An arrangement of a layer of the material of the reference electrode 5', of a layer of nonwoven 8' and of a layer of a material of a protective electrode 6' is placed one on top of another and rolled up helically together, the layer of the material of the protective electrode 6' forming the outermost layer of the overall arrangement. The nonwoven structure ensures effective wetting of the electrode surfaces by the electrolyte solution and makes it possible at the same time that the protective electrode is arranged sufficiently close to the reference electrode to ensure the effective shielding of the reference electrode and the depletion according to the present invention in its vicinity.

Figure 3:
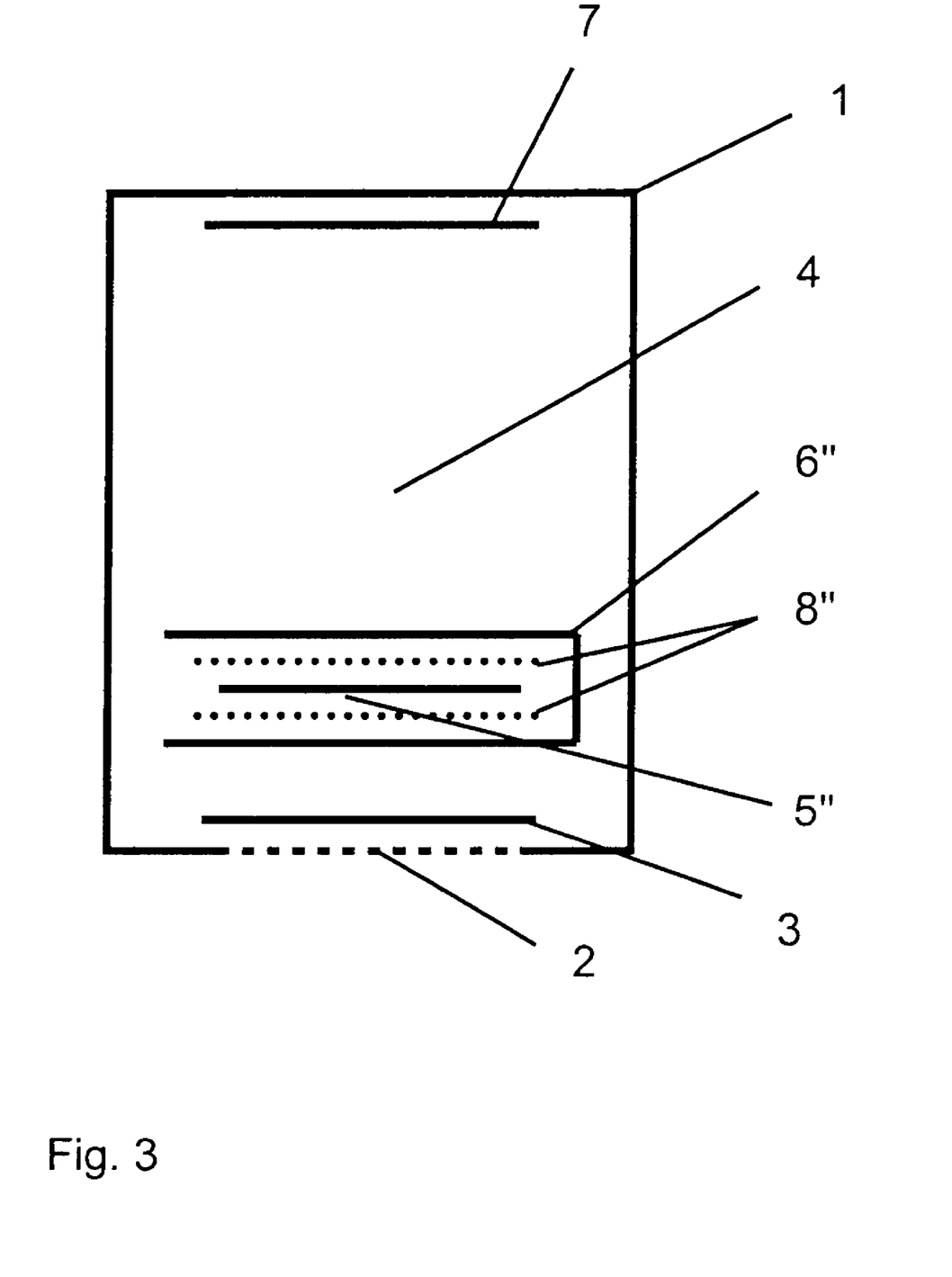
FIG. 3 is a sectional view through a three-electrode sensor with a reference electrode designed as a sandwich structure.

FIG. 3 shows, analogously to FIG. 1, a sensor according to the present invention, in which the reference electrode is designed as a sandwich structure. A layer of the material of the reference electrode 5'', which is surrounded by a layer of a nonwoven material 8'' each, is located in the interior of the sandwich structure and the protective electrode 6'' arranged around the reference electrode in the form of a folded-over foldable pocket, the nonwoven material 8'' being in turn surrounded by a layer each of the material of the protective electrode 6''. Especially effective shielding of the reference electrode can be achieved in this manner. Moreover, such electrodes can be adapted without problems to the cross section of the sensor housing 1 and, in case of sufficient dimensioning, they ensure in this manner the effective reduction of the diffusion of substances to be detected from the region of the measuring electrode 3 into the region of the auxiliary electrode 7, as a result of which "cross-talk" is effectively prevented from occurring.

Figure 4:
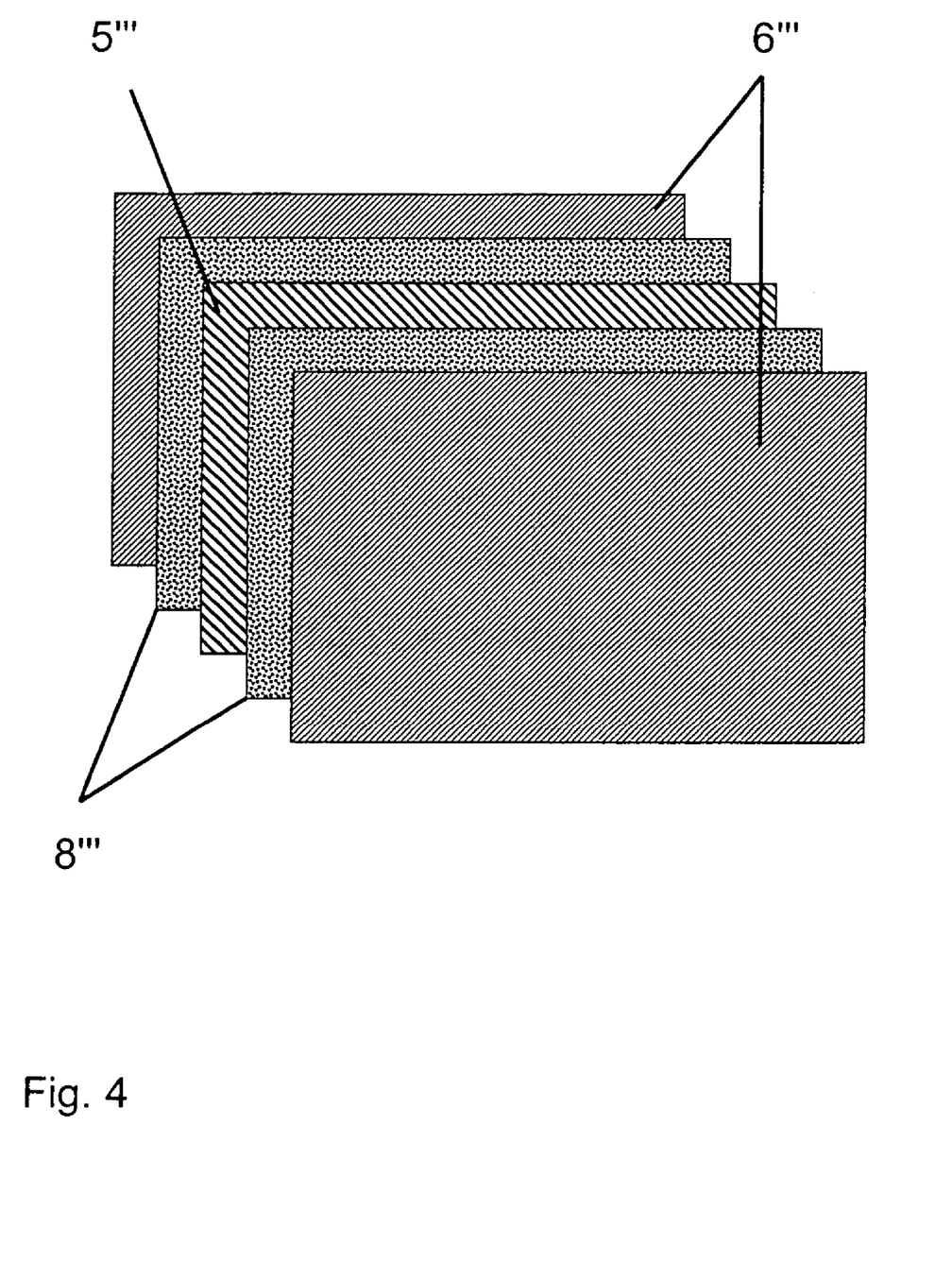
FIG. 4 is an exploded view of a detail of a reference electrode according to the present invention, which is designed as a sandwich structure.

FIG. 4 shows an exploded view of a detail from a reference electrode according to the present invention which has a sandwich design. A layer of the material for the reference electrode 5''' is arranged in the central area. This is surrounded on both sides by a one-layer nonwoven material 8''' each. A layer each of the material of the protective electrode 6''' is located in front of the nonwoven.

Figure 5:
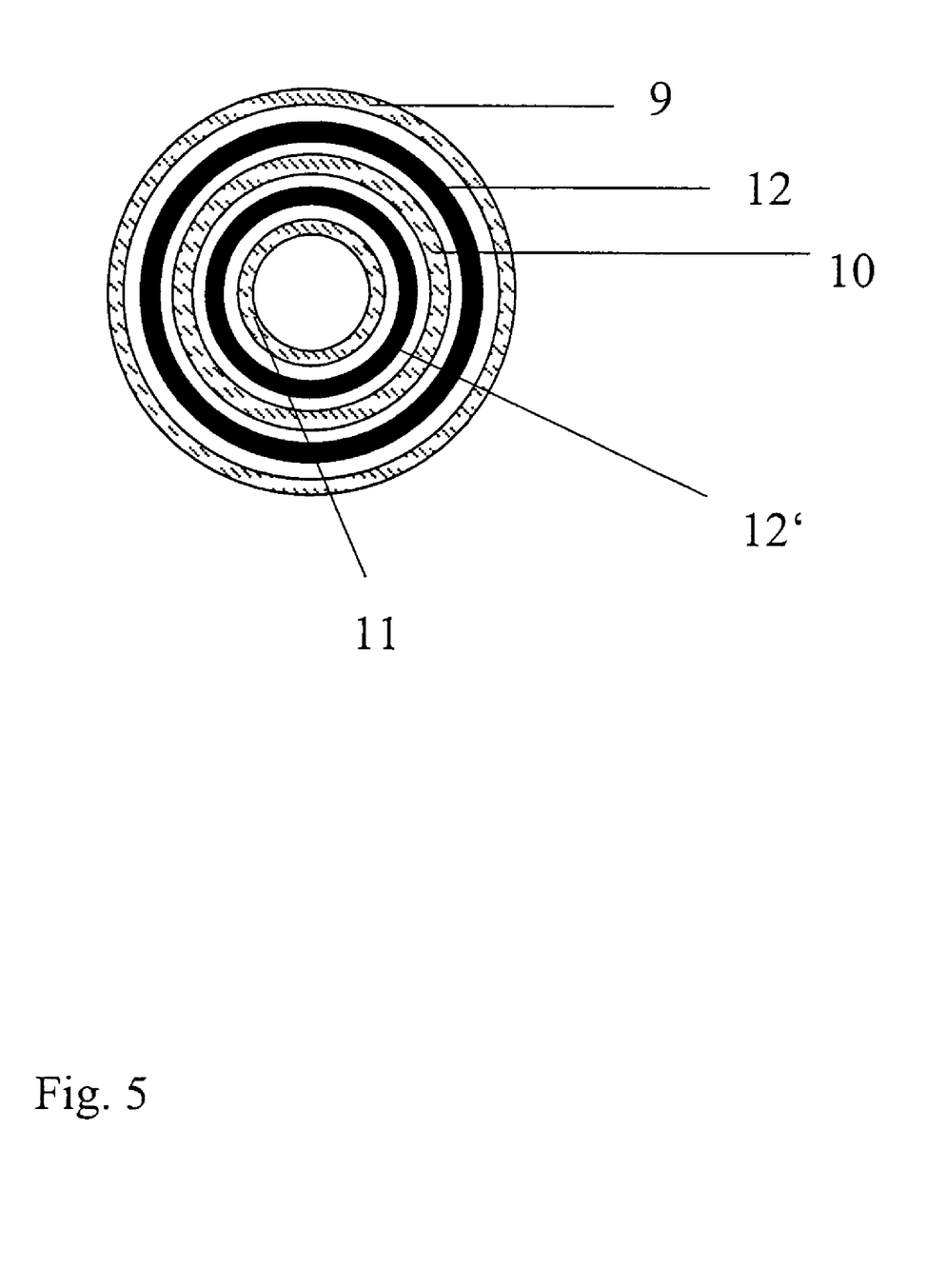
FIG. 5 is a sectional view of an electrode arrangement according to the present invention with cylinder electrodes.

FIG. 5 shows a sectional view of an electrode arrangement according to the present invention with cylinder electrodes, which are arranged concentrically. An outer cylinder 9 forms the measuring electrode, a middle cylinder 10 forms the reference electrode, and an inner cylinder 11 forms the auxiliary electrode. A cylindrical protective electrode 12, 12' each is arranged between the electrodes. The cylindrical protective electrodes 12, 12' are permeable to the electrolyte, are approximately at the potential of the measuring electrode and shield the reference electrode against the effect of substances that cause changes in the potential.

Figure 6:
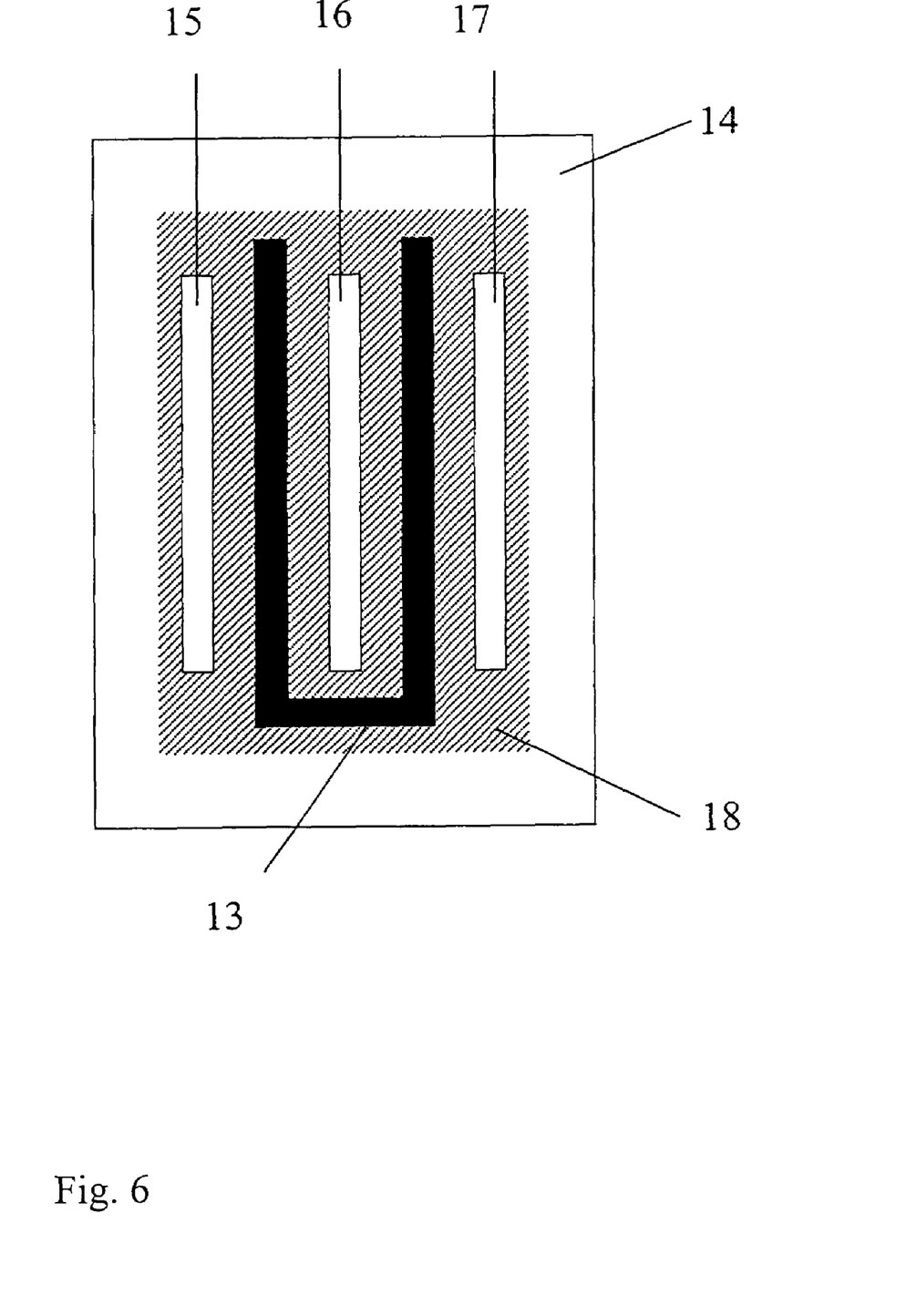
FIG. 6 is a planar sensor according to the present invention with a U-shaped protective electrode.

FIG. 6 shows a planar sensor according to the present invention with a U-shaped protective electrode 13. Such sensors usually enclose planar electrodes, one of which acts as a measuring electrode 15, one as a reference electrode 16 and one as an auxiliary electrode 17, in a flat, flexible housing 14. These electrodes communicate with one another via an electrolyte 18, which extends essentially two-dimensionally. A U-shaped planar protective electrode 13 according to the present invention opens up an advantageous possibility of blocking the diffusion paths to the reference electrode 16 for substances that affect the reference potential. Nearly complete shielding of the reference electrode 16 against these substances can be achieved due to the two-dimensional extension of the electrolyte 18, without the reference electrode 16 having to be completely enveloped by the protective electrode 13. Such sensors can be manufactured in an especially simple and advantageous manner.

Figure 7:
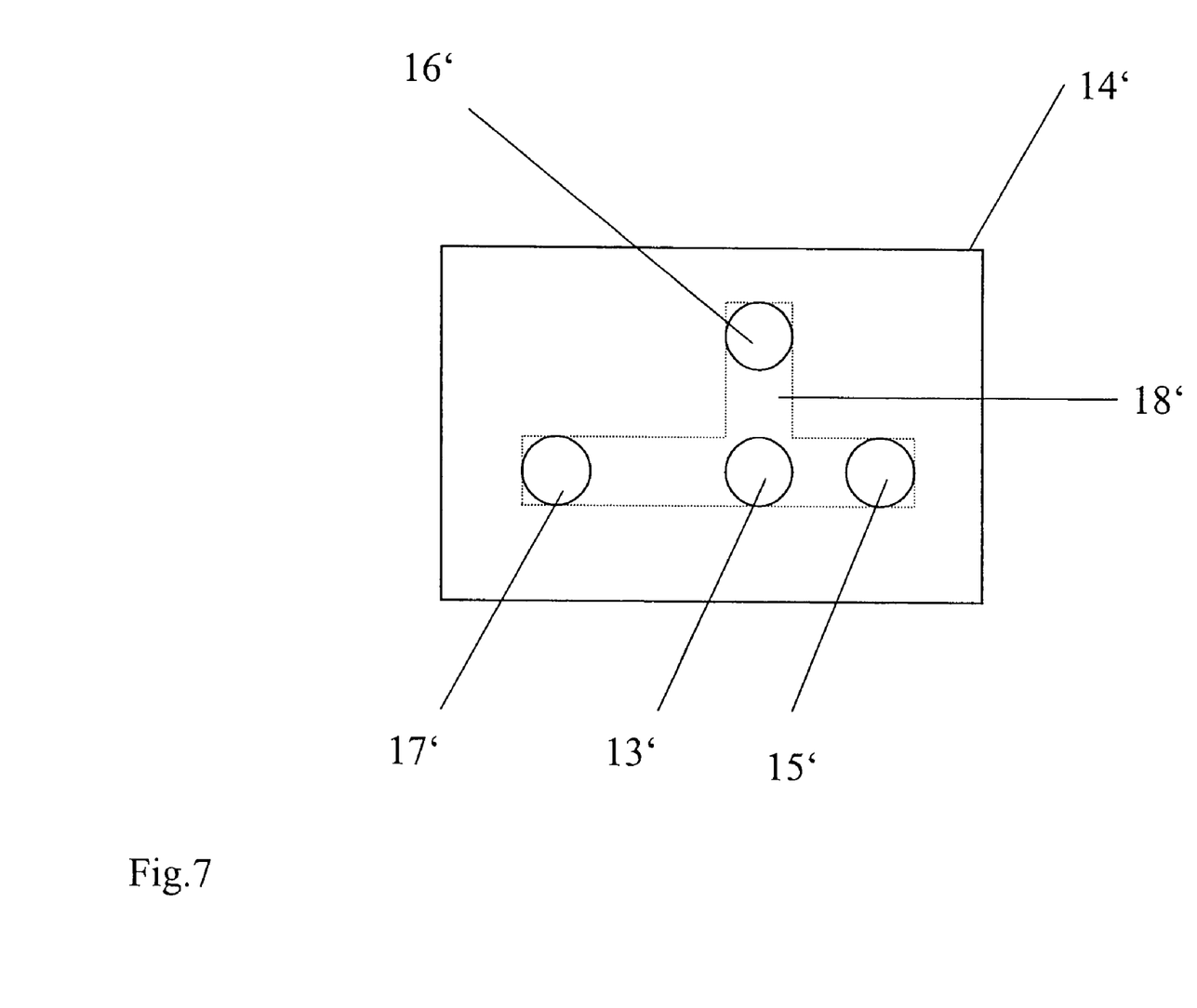
FIG. 7 is a planar sensor with round electrodes.

FIG. 7 shows a planar sensor with round electrodes. The parts of the sensor housing 14' are connected with one another such that only a narrow, strip-shaped, singly branched area 18 can be filled with electrolyte. Round electrodes acting as a measuring electrode 15', a reference electrode 16' and an auxiliary electrode 17' are arranged at the ends of this area 18. A round protective electrode 13' is arranged in the area of branching. The diameter of this electrode is selected to be such that the reference electrode 16' is not cut off completely from the electrolyte path to the other electrodes. If the protective electrode 13' is approximately at the potential of the measuring electrode, it nevertheless generates a depleted area, which separates the electrolyte areas in front of the electrodes 15', 16', 17' from one another in respect to the diffusion of the species to be depleted and thus it ensures the desired shielding of the reference electrode 16' and at the same time effectively prevents "cross-talk" from occurring between the auxiliary electrode 17' and the measuring electrode 15'.

Figure 8:
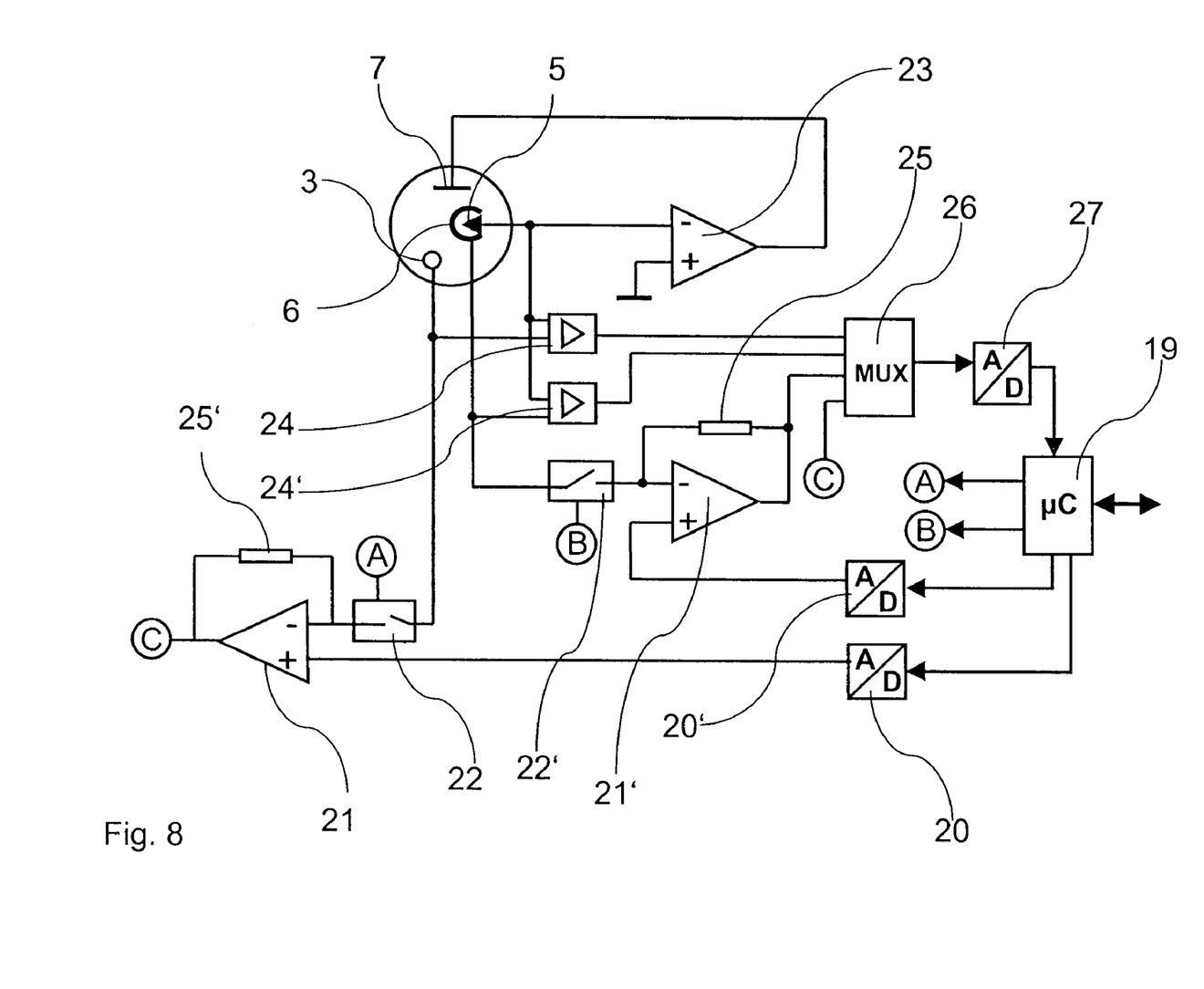
FIG. 8 is a circuit diagram of an exemplary circuit with a sensor according to the present invention.

FIG. 8 shows a circuit diagram of an exemplary circuit with a sensor according to the present invention. Continuous lines are shown as being partially interrupted, and ends that belong together are designated with the same letters in a circle. Besides an auxiliary electrode 7, a measuring electrode 3 and a reference electrode 5, the sensor has a protective electrode 6, which is connected as the measuring electrode 3 but can be operated independently from same and surrounds the reference electrode 5 in a pocket-like manner. The measuring electrode 3 and the protective electrode 6 can be set at settable potentials, which are preset by a microcontroller 19, the digital output values of the microcontroller 19 ensuring a stable voltage at the measuring electrode 3 and at the protective electrode 6 via a D/A converter 20, 20' each and an operational amplifier 21, 21'. The power supply of the measuring electrode 3 and of the protective electrode 6 can be interrupted by switches 22, 22', which can likewise be actuated by the microcontroller 19, in order to make it possible to use different modes of operation. Another operational amplifier 23 guarantees that the reference potential at the reference electrode 5 corresponds to ground in terms of circuitry.

The voltage difference between the measuring electrode 3 and the reference electrode 5 can be determined by the instrument amplifier 24, the voltage difference between the protective electrode 6 and the reference electrode 5 can be determined by the instrument amplifier 24', and the current flow through the particular measuring electrode 3 and protective electrode 6 can be determined from the voltage drop over the particular precision resistors 25, 25'. All the voltages to be measured can be sent to the microcontroller 19 for processing via a multiplexer 26 and an A/D converter 27. Besides the intended use of sensors according to the present invention, measurements which are necessary for the optimization of the mode of operation of the protective electrode can be carried out with such a circuit in an especially advantageous manner.

While specific embodiments of the invention have been shown and described in detail to illustrate the application of the principles of the invention, it will be understood that the invention may be embodied otherwise without departing from such principles.

What is claimed is:

1. An electrochemical sensor, comprising:
a housing body with an opening;
a diffusion membrane covering said opening;
an electrolyte in said housing body;
a measuring electrode in said housing body adjacent to said opening and in contact with said electrolyte;
a reference electrode consisting of a carbon containing material, said reference electrode being in said housing body in contact with said electrolyte;
a protective electrode in said housing body in contact with said electrolyte and arranged adjacent to said reference electrode at least partially surrounding said reference electrode for shielding said reference electrode against substances that would lead to a change in a reference potential when reaching said reference electrode;
an auxiliary electrode;
a mediator material in said housing body for essentially determining an electrical potential of said reference electrode; and
a sensor circuit connected to each of said measuring electrode, said reference electrode, said protective electrode and said auxiliary electrode for setting said measuring electrode at one of settable potentials and for setting the protective electrode at one of settable potentials and for determining a voltage difference between said measuring electrode and said reference electrode, for determining a voltage difference between said protective electrode and said reference electrode, and for determining a current flow through said measuring electrode and through said protective electrode, and including a microcontroller for setting said settable potentials and for receiving signals representing each said determined voltage difference and said current flow.

2. An electrochemical sensor in accordance with claim 1, wherein said protective electrode is at a potential that deviates from a potential at which said measuring electrode is maintained by at most +/−100 mV.

3. An electrochemical sensor in accordance with claim 1, wherein a surface of said reference electrode is partially covered with a material that has a barrier action against substances that would lead to a change in a reference potential when reaching said reference electrode.

4. An electrochemical sensor in accordance with claim 1, wherein said reference electrode is located on a plastic carrier, which seals said reference electrode on at least one side.

5. An electrochemical sensor in accordance with claim 1, wherein said reference electrode is further shielded at least partially by an ion exchange membrane.

6. An electrochemical sensor in accordance with claim 1, wherein said reference electrode is surrounded essentially by said protective electrode that is permeable to electrolyte.

7. An electrochemical sensor in accordance with claim 1, wherein the sensor is designed as a flat sensor with nearly two-dimensional diffusion paths, said protective electrode being placed such that it blocks the diffusion paths to said reference electrode for substances affecting the reference potential.

8. An electrochemical sensor in accordance with claim 1, wherein at least one layer of nonwoven material, which ensures the flat contact of both electrodes with the electrolyte, is arranged between said protective electrode and said reference electrode.

9. An electrochemical sensor in accordance with claim 1, wherein said reference electrode consists essentially of a catalytically active precious metal.

10. An electrochemical sensor in accordance with claim 1, wherein said reference electrode consists essentially of diamond-like carbon.

11. An electrochemical sensor in accordance with claim 1, wherein said reference electrode consists essentially of doped diamond.

12. An electrochemical sensor in accordance with claim 1, wherein said reference electrode consists essentially of "carbon nanotubes."

13. An electrochemical sensor in accordance with claim 1, wherein said protective electrode consists essentially of platinum.

14. An electrochemical sensor in accordance with claim 1, wherein said measuring electrode and said reference electrode consist essentially of the same material or materials.

15. An electrochemical sensor in accordance with claim 1, wherein said reference electrode and said protective electrode together form a sandwich structure comprising a layer of the material of the reference electrode surrounded by nonwoven material including a layer of a nonwoven material above the reference electrode and a layer of nonwoven material below the reference electrode and the protective electrode is arranged folded-over around the reference electrode and layers of nonwoven material in the form of a pocket having an open end, open to the electrolyte and with the nonwoven material in contact with said electrolyte.

16. An electrochemical sensor in accordance with claim 1, wherein:
said reference electrode and said protective electrode together form a sandwich structure comprising a layer of the material of the reference electrode surrounded by nonwoven material including a layer of a nonwoven material above the reference electrode and a layer of nonwoven material below the reference electrode and the protective electrode is arranged folded-over around the reference electrode and layers of non woven material in the form of a pocket having an open end, open to the electrolyte and with the non woven material in contact with said electrolyte; and
said microcontroller and said sensor circuit set said protective electrode at a potential that deviates from a potential at which said measuring electrode is maintained by at most +/−100 mV.

* * * * *